United States Patent [19]
Mader et al.

[11] Patent Number: 5,512,483
[45] Date of Patent: Apr. 30, 1996

[54] EXPRESSION VECTORS RESPONSIVE TO STEROID HORMONES

[75] Inventors: Sylvie Mader; John H. White, both of Montreal, Canada

[73] Assignee: McGill University, Quebec, Canada

[21] Appl. No.: 66,397

[22] Filed: May 21, 1993

[51] Int. Cl.$^6$ .......................... C12N 15/63; C12N 15/79
[52] U.S. Cl. ....................................... 435/320.1; 536/24.1
[58] Field of Search ............................. 435/320.1, 91.41, 435/69.1, 69.4; 530/350; 536/24.1

[56] References Cited

PUBLICATIONS

Mader et al., "A Steroid–inducible promoter for the controlled overexpression of cloned genes in eukaryotic cells", PNAS 90:5603, 1993.
Philpott et al., "The bifunctional iron–responsive element binding protein/cytosolic aconitase . . . binding and regulation", PNAS 91:7321, 1994.
Samaniego et al., "Molecular Characterization of a Second Iron–responsive Element Binding Protein, Iron Regulatory Protein 2", J. Biol. Chem., 269(49) 30904, 1994.
Strahle et al., "Synergistic action of the glucocorticoid receptor with transcription factors", The EMBO Journal, 7(11):3389–3395, 1988.
White et al., "A Simple and Sensitive High–Throughput Assay for Steroid Agonists and Antagonists", Bio/Technology 12:1003, 1994.
Buratowski et al., "Five Intermediate Complexes in Transcription Initiation by RNA Polymerase II", 56 Cell 549, 1989.
Mitchel and Tjian, "Transcriptional Regulation in Mammalian Cells by Sequence–Specific DNA Binding Proteins", 245 Science 371, 1989.
Ptashne and Gann, "Activators and targets", 346 Nature 329, 1990.
Lewin, "Commitment and Activation at Pol II Promoters: A Tail of Protein–Protein Interactions", 61 Cell 1161, 1990.
Zenke et al., "Multiple sequence motifs are involved in SV40 enhancer function", 5 EMBO J. 387, 1986.
Jantzen et al., "Cooperativity of Glucocorticoid Response Elements Located Far Upstream of the Tyrosine Aminotransferase Gene", 49 Cell 29, 1987.
Green and Chambon, "Nuclear receptors enhance our understanding of transcription regulation", 4 Trends in Genet 309, 1988.
Evans, "The Steroid and Thyroid Hormone Receptor Superfamily", 240 Science 889, 1988.
Wahli and Martinez, "Superfamily of Steroid nuclear receptors: positive and negative regulators of gene expression", 5 FASEB J. 2243, 1991.
Gronemeyer, "Transcription Activation by Estrogen and Progesterone Receptors", 25 Ann. Rev. Genet. 89, 1991.
Montminy et al., "Regulation of cAMP–inducible genes by CREB", 13 Trends in Neurolog. Sciences 184, 1990.
Angel and Karin, "The role of Jun, Fos and the AP–1 complex in cell=proliferation and transformation", 1072 Biochim. Biophys. Acta. 129, 1991.

Lin et al., "Casein Kinase II Is a Negative Regulator of c–Jun DNA Binding and AP–1 Activity", 70 Cell 777, 1991.
Bauerle, "The inducible transcription activator NF–kB: regulation by distinct protein subunits", 1072 Biochin. Biophys. Acta. 63, 1991.
Hunter and Karin, "The Regulation of Transcription by Phosphorylation", 70 Cell 375, 1992.
Krust et al., "The chicken oestrogen receptor sequence: homology with v–verbA and the human oestrogen and glucocorticoid receptors", 5 EMBO J. 891, 1986.
Giguere et al., "Functional Domains of the Human Glucocorticoid Receptor", 46 Cell 645, 1986.
Kumar et al., "Functional Domains of the Human Estrogen Receptor", 51 Cell 941, 1987.
Kumar and Chambon, "The Estrogen Receptor Binds Tightly to its Responsive Element as a Ligand–Induced Homodimer", 55 Cell 145, 1988.
Green and Chambon, "Oestradiol induction of a glucocorticoid–responsive gene by a chimaeric receptor", 325 Nature 75, 1987.
Evans and Hollenberg, "Zinc fingers: Gilt by Association", 52 Cell 1, 1988.
Schwabe et al., "Solution structure of the DNA–binding domain of the oestrogen receptor", 348 Nature 458, 1990.
Hard et al., "Solution Structure of the Glucocorticoid Receptor DNA–Binding Domain", 249 Science 157, 1990.
Luisi et al., "Crystallographic analysis of the interaction of the glucocorticoid receptor with DNA", 352 Nature 497, 1991.
Mader et al., "Three amino acids of the oestrogen receptor are essential to its ability to distinguish an oestrogen from a glucocorticoid–responsive element", 338 Nature 271, 1989.
Umesomo and Evans, "Determinants of Target Gene Specificity for Steroid/Thyroid Hormone Receptors", 57 Cell 1139, 1989.
Danielsen et al., "Two Amino Acids within the Knuckle of the First Zinc Finger Specify DNA Response ELement Activation by the Glucocorticoid Receptor", 57 Cell 1131, 1989.
Tora et al., "The Human Estrogen Receptor Has Two Independent Nonacidic Transcriptional Activation Functions", 59 Cell 447, 1989.

(List continued on next page.)

Primary Examiner—Stephen G. Walsh
Assistant Examiner—John D. Ulm
Attorney, Agent, or Firm—Lyon & Lyon

[57] ABSTRACT

Expression vector adapted for expression of cloned genes in an animal cell comprising a steroid responsive promoter, the promoter consisting essentially of a plurality of glucocorticoid response elements (GREs), a TATA box, and an initiator element containing a transcriptional initiator site located from 20 to 50 bases from the TATA box, the promoter lacking upstream elements which bind nuclear factor I, and the vector further comprising a restriction endonuclease site downstream from the promoter for insertion of DNA to be expressed from the promoter, wherein the DNA is expressed from the vector in an animal cell.

10 Claims, 1 Drawing Sheet

PUBLICATIONS

Martinez et al., "The estrogen–responsive element as an inducible enhancer: DNA sequence requirements and conversion to a glucocorticoid–responsive element", 6 *EMBO J.* 3719, 1987.

Burch et al., "Two Functional Estrogen Response Elements Are Located Upstream of the Major Chicken Vitellogenin Gene", 8 *Mol. Cell. Biol.* 1123, 1988.

Ponglikitmongkol et al., "Synergistic activation of transcription by the human estrogen receptor bound to tandem responsive elements", 9 *EMBO J.* 2221, 1990.

Schule et al., "Cooperativity of the glucocorticoid receptor and the CACCC–box binding factor", 332 *Nature* 87, 1988.

Lee et al., "Glucocorticoids regulate expression of dihydrofolate reductase cDNA in mouse mammary tumour virus chimaeric plasmids", 294 *Nature* 259, 1984.

Ucker et al., "Mammary Tumor virus DNA Contains Sequences Required for Its Hormone–Regulated Transcription", 27 *Cell* 257, 1981.

Metzger et al., "The human oestrogen receptor functions in yeast", 334 *Nature* 31, 1988.

Payvar et al., "Sequence–Specific Binding of Glucocorticoid Receptor to MTV DNA at Sites within and Upstream of the Transcribed Region", 35 *Cell* 381, 1983.

Scheidereit et al., "The glucocorticoid receptor binds to defined nucleotide sequences near the promoter of mouse mammary tumour virus", 304 *Nature* 749, 1983.

Smale and Baltimore, "The Initiator as a Transcription Control Element", 57 *Cell* 103, 1989.

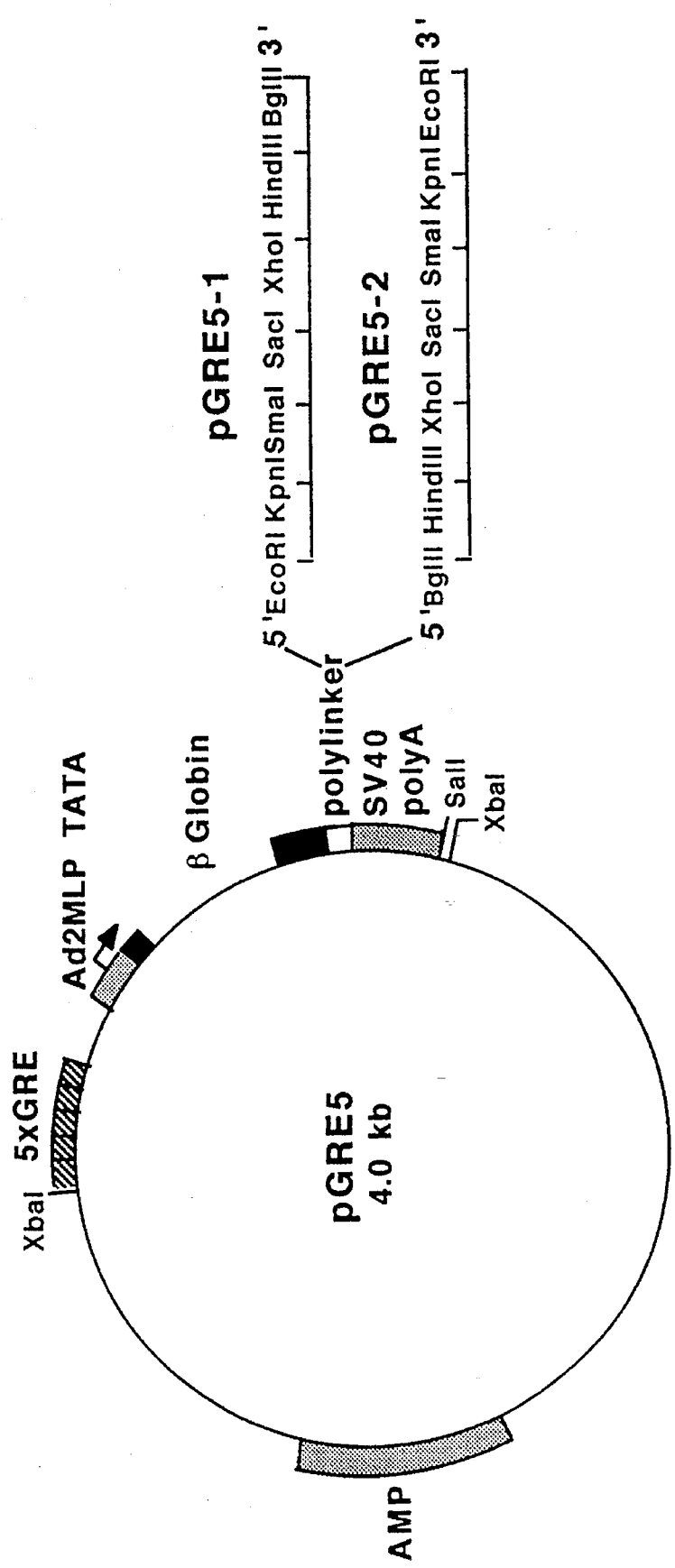

EXPRESSION VECTORS RESPONSIVE TO STEROID HORMONES

BACKGROUND OF THE INVENTION

This invention relates to vectors suitable for expression of a desired protein in an animal cell in response to the presence of one or more steroid hormones.

Transcription of eukaryotic class II genes is regulated by a complex array of trans-acting transcription factors which bind to specific DNA sequences in the promoter of a target gene. On most promoters transcriptional preinitiation complexes are assembled at the TATA box which is generally located 25–30 base pairs (bp) 5' to the site of initiation (Buratowski et al., 56 Cell 549, 1989). Preinitiation complex assembly is regulated, in part, by factors which bind to DNA sequences known as enhancers most often situated at varying distances upstream of the TATA box/initiation site (Mitchel and Tjian, 245 Science 371, 1989; Ptashne and Gann, 346 Nature 329, 1990; and Lewin, 61 Cell 1161, 1990). Enhancers can be located immediately adjacent to the site of transcriptional initiation or several kilo-bases distant from it (Zenke et al., 5 EMBO J. 387, 1986; and Jantzen et al., 49 Cell 29, 1987). The activity of enhancer factors can be directly responsive to specific intercellular signals or indirectly via intracellular transduction pathways (Green and Chambon, 4 Trends in Genet 309, 1988; Evans, 240 Science 889, 1988; Wahli and Martinez, 5 FASEB J. 2243, 1991; Gronemeyer, 25 Ann. Rev. Genet. 89, 1991; Montiminy et al., 13 Trends in Neurolog. Sciences 184, 1990; Angel and Karin, 1072 Biochim. Biophys. Acta. 129, 1991; Lin et al., 70 Cell 777, 1991; Bauerle, 1072 Biochim. Biophys. Acta. 63, 1991; and Hunter and Karin, 70 Cell 375, 1992).

The nuclear receptors represent a family of transcriptional enhancer factors which act by binding to specific DNA sequences found in target promoters known as response elements (REs) (Green and Chambon, supra; Evans, supra; Wahli and Martinez, supra; and Gronemeyer, supra). Specific members of the nuclear receptor family represent the primary intracellular targets for small lipid soluble ligands such as steroid and thyroid hormones, retinoids and vitamin D3, and as such act as ligand-inducible transcription factors. Sequence comparisons (Krust et al., 5 EMBO J. 891, 1986) and structure-function analyses (Giguere et al., 46 Cell 645, 1986; Kumar et al., 51 Cell 941, 1987; Kumar and Chambon, 55 Cell 145, 1988; and Green and Chambon, 325 Nature 75, 1987) have shown that the receptors are composed of a series of conserved domains. The most highly conserved domain is the DNA binding domain located in region C (Krust et al., supra; Green and Chambon supra; and Evans and Hollenberg, 52 Cell 1, 1988) containing a 66–68 amino acid core composed of two zinc fingers (Schwabe et al., 348 Nature 458, 1990; Hard et al., 249 Science 157, 1990; and Luisi et al., 352 Nature 497, 1991) which is essential for recognition of REs. Three amino acids adjacent to the N-terminal zinc finger of the DNA binding domain, known as the P-box, are critical for DNA sequence recognition (Mader et al., 338 Nature 271, 1989; Umesomo and Evans, 57 Cell 1139, 1989; and Danielson et al., 57 Cell 1131, 1989). A subfamily composed of the glucocorticoid, mineralocorticoid, progesterone and androgen receptors contain Gly, Ser and Val at discriminatory positions of the P-box and recognize AGAACA half-sites arranged in a palindrome with a 3 bp spacer region (Mader et al., supra; Umesomo and Evans, supra; and Danielson et al., supra).

The ligand binding domain, located C-terminal to the DNA binding domain in region E, is less well conserved among the receptors and contains a ligand-inducible transcriptional activation function (Green and Chambon, supra; Evans, supra; Wahli and Martinez, supra; Gronemeyer, supra; Giguere et al., 46 Cell 645, 1986; and Kumar et al., 51 Cell 941, 1987). Transcriptional activating domains have also been identified in the poorly conserved N-terminal A/B regions of the glucocorticoid and estrogen receptors (Giguere et al., supra; Kumar et al., supra; and Tora et al., 59 Cell 447, 1989).

Response elements are often found in multiple arrays, usually located upstream of the site of transcriptional initiation (Jantzen et al., supra; Martinez et al., 6 EMBO J. 3719, 1987; and Burch et al., 8 Mol. Cell. Biol. 1123, 1988). Functional analysis of two glucocorticoid response elements (GREs) located far upstream of the rat tyrosine aminotransferase (TAT) gene has shown that they combine synergistically to mediate transcriptional activation by the glucocorticoid receptor (GR) (Jantzen et al., supra). The two nonconsensus estrogen response elements (EREs) of the Xenopus vitellogenin B1 gene are virtually inactive in isolation, but together mediate estrogen-dependent transcriptional activation in transiently transfected cells (Martinez et al., supra). The degree of synergism between paired EREs or GREs is dependent on their sequence, the spacing between them and their distance from the TATA box of the promoter (Ponglikitmongkol et al., 9 EMBO J. 2221, 1990; and Schule et al., 332 Nature 87, 1988). Several studies have also shown that nuclear receptors and other classes of transcriptional regulators can combine to activate transcription synergistically (Tora et al., supra; and Schule et al., supra).

Promoters activated by specific inducible nuclear receptors are well suited for eukaryotic expression vectors since expression of genes can be regulated simply by controlling the concentration of ligand present in growth media (Kumar supra; Lee et al., 294 Nature 259, 1984; Ucker et al., 27 Cell 257, 1981; and Metzger et al., 334 Nature 31, 1988). Glucocorticoid-inducible promoters such as that of the long terminal repeat of the mouse mammary tumor virus (MMTV) have been widely used in this regard because the GR is expressed in a wide variety of mammalian cell types. The MMTV GRE is composed largely of a series of half-sites (Payvar et al., 35 Cell 381, 1983; and Scheidereit et al., 304 Nature 749, 1983). While the MMTV promoter can be induced by ligand-bound receptors for both glucocorticoids and progesterone when introduced into cells by transient transfection, it is selectively responsive to glucocorticoids when propagated on an episomal vector (Hager and Archer, in "Nuclear Hormone Receptors: Molecular Mechanisms, Cellular functions and Clinical Abnormalities," (Parker, M. G. ed.), Academic Press Ltd. 217, 1991). It is proposed that the nucleosome structure of the episomal DNA selectively inhibits access of the progesterone receptor to the response element.

Schena et al., 88 Proc. Natl. Acad. Sci. USA 10421, 1991, describe a steriod inducible expression system for plant cells in which six 26-base pair GREs are fused upstream of a plant site of transcription initiation with a plant TATA box as the sole promoter element. By providing glucocorticoid receptor and glucocorticoid hormone, inducible expression of a gene in a plant cell was achieved.

SUMMARY OF THE INVENTION

Applicant has constructed a mammalian expression vector containing a synthetic promoter composed of several high affinity glucocorticoid response elements placed upstream of a minimal promoter TATA region. In transiently transfected HeLa cells in the presence of dexamethasone, one of these promoters was at least 50-fold more efficient than the mouse mammary tumor virus long terminal repeat in expressing bacterial chloramphenicol acetyl-transferase (CAT) activity. When the vector was introduced stably into the HeLa cell genome CAT activity was induced from 10 to more than 50-fold by dexamethasone in 6 of 8 responsive clones. The levels of both basal and induced expression varied from one clone to the next, probably due to an effect of chromosomal location on promoter activity. When propagated stably in HeLa cells in an Epstein-Barr virus episomal vector, the promoter was greater than 50-fold inducible, and its activity was strictly dependent on the presence of dexamethasone. The promoter when stably propagated in HeLa cells was inducible by progesterone in the presence of a transiently transfected progesterone receptor expression vector. These promoters are widely applicable for the strictly controlled high level expression of target genes in eukaryotic cells that contain either the glucocorticoid or progesterone receptors.

Thus, in the first aspect, the invention features an expression vector adapted to replicate in animal cells (i.e., having the requisite animal origin of replication), which includes a plurality of glucocorticoid responsive elements (GREs) and a minimal promoter. Applicant has discovered that the use of such a minimal promoter with such GREs provides a promoter responsive not only to glucocorticoid but also to other receptors including progesterone, androgen, and mineralocorticoid receptors when that vector is stably integrated within a host cell.

By "minimal promoter" is simply meant a promoter that consists, essentially, of a plurality of the glucocorticoid responsive elements, a TATA box, and an initiator element containing a transcriptional initiation site (Smale and Baltimore, 57 *Cell* 103, 1989) which is of mammalian or vital origin) located about 20 to 50 bases from the TATA box. No other upstream elements are provided, for example, those which bind nuclear factor I or other such upstream element factors. The vector further includes a restriction endonuclease site downstream from the promoter for insertion of DNA to be expressed from that promoter. Such a promoter is of viral or mammalian origin.

By "glucocorticoid responsive element" is meant an element having at least one-half consensus sequence, where that consensus sequence is 5' AGAACANNNTGTTCT 3', (where N is any nucleotide base), or any equivalent sequence which is able to bind the above receptors for glucocorticoids, progesterones, androgen, or mineralocorticoid. Such GREs may be synthetically prepared or may be isolated from naturally occurring GREs. Thus, the GRE is simply a family of related DNA sequences which are recognized by one or more of the above receptors. Those in the art will recognize that such GREs can be readily synthesized or discovered using standard binding assays for detection of DNA elements able to bind the above receptors. (Schmid et al., 8 *EMBO Journal* 2257, 1989.)

By "TATA box" is simply meant a DNA binding site of mammalian or viral origin for the TATA box binding protein referred to as TFIID, which is the first protein found in transcriptional preinitiation complex assembly. Such a box, generally, has the nucleotide base sequence TATA (hence its name) which may be followed by another TATA sequence or by AAA. Those of ordinary skill in the art will recognize other variants of this sequence. All that is necessary in the invention is that the TATA box be able to bind the TFIID protein such that transcriptional initiation can occur. As noted, this box is generally placed between 20 and 50 bases from a transcriptional initiation site, which is the point at which transcription will occur. Such sites are well known in the art.

In preferred embodiments, the TATA box is positioned 25 to 30 bases from the initiation site; the GREs are placed upstream from the TATA box; and at least two GREs are placed within 100 bases of this TATA box. In a more preferred embodiment, at least 5 GREs are provided within the vector, all located within about 500 bases of the TATA box. Preferably the GREs are position between 20 and 60 bases apart, most preferably between 30 and 40 bases apart. In the most preferred embodiment, the expression vector includes a promoter which is responsive to not only glucocorticoid receptors but also progesterone, androgen, and mineralocorticoid receptors, when the vector is stably integrated within a genome.

In a related aspect, the invention features a method for expressing a desired protein in response to one or more of a glucocorticoid, progesterone, androgen, and mineralocorticoid, by providing a suitable DNA sequence encoding the desired protein within an expression vector described above, and providing that vector within a suitable expression system such as a mammalian cell, either in an integrated or nonintegrated fashion.

The advantages of the presently described vectors include the following. Since the vector includes a minimal promoter composed of only a TATA box, an initiator element and multiple GREs, and (unlike the MMTV promoter) lacks binding sites for other regulatory transcription factors, its activity is easily controlled solely by regulating the concentration of steroid hormone in the growth media. In addition, since the promoter is exclusively regulated by the activity of hormone bound steroid receptors there is no detectable activity when the promoter is propagated under controlled conditions in the absence of steroid. This is particularly important when one wants controlled expression of a gene whose product is lethal to the cell when expressed constitutively. Unlike MMTV, the promoter maintains responsiveness to progesterone as well as glucocorticoids when stably propagated in cells, and the promoter is more highly inducible by glucocorticoids than MMTV.

Other features and advantages of the invention will be apparent from the following description of the preferred embodiments thereof, and from the claims.

DESCRIPTION OF THE PREFERRED EMBODIMENTS

The drawing will first briefly be described.
Drawing
The FIGURE is a representation of pGRE5 expression vectors of this invention.

The following methods were used to prepare vectors of this invention. This exemplifies the invention but is not limiting to the invention. Those in the art can readily construct equivalent vectors within the pending claims using similar or equivalent techniques.
Vectors
Previous studies with estrogen-inducible minimal promoters have shown that a TATA region and one or more estrogen response elements are sufficient for a transcriptional response to estrogen in the presence of ligand-bound estrogen receptor (Ponglikitmongkol et al., supra). In HeLa cells, promoters based on the Ad2MLP TATA region (−34 to +33) have undetectable basal activity in the absence of inducer (Ponglikitmongkol et al., supra), and are therefore potentially useful in inducible expression vectors. Here, we constructed a series or glucocorticoid-responsive minimal promoters composed of the Ad2MLP TATA region and one or more GREs from the rat TATA gene (Jantzen et al., supra) placed upstream of a rabbit β-globin reporter gene in the plasmid pAL10 (Ponglikitmongkol et al., supra).

Specifically, a 35 bp oligonucleotide containing the rat TAT GRE flanked by BamHI and BglII ends was concatemerized in the presence of BamHI, BglII and T4 DNA ligase and bands corresponding to dimers and pentamers were purified from a 5% polyacrylamide gel for insertion into the BglII site (−65) of pAL10 (Ponglikitmongkol et al., supra). Recombinants containing a single GRE, or head-to-tail direct repeats of GREs conserving the BglII site a −65 were isolated to create GRE/pAL10, GRE2/pAL10 and GRE5/pAL10. GRES/pAL10 was then modified to remove unnecessary sequence and restriction sites, and a polylinker containing sites for EcoRI, KpnI, SmaI, SacI, XhoI, HindIII, and BglII was inserted in either orientation to create GRE5-1 and pGRE5-2 (see FIG.).

The rabbit β-globin sequence of pGRE5 runs from the naturally occurring BamHI site to the EcoRI site and contains the second globin intron (Breathnach and Harris, 11 *Nucleic Acids Research* 7119, 1983). To create GRE5/CAT recombinants, the BglII-SmaI fragment from pBLCAT8+ (Klein-Hitpass et al., 46 *Cell* 1053, 1986), containing the CAT gene was excised and inserted in the pGRE5-1 or pGRE5-2 polylinker digested with SmaI and BglII in the sense and antisense orientations, respectively. The pGRE1tkCAT and pGRE2tkCAT plasmids were created by inserting one or two perfectly palindromic GREs upstream of the Herpes Simplex virus thymidine kinase promoter in pBLCAT8+. To create p220.2-GRE5/CAT recombinants, the XbaI-SalI fragment (see FIG.) from the pGRE5/CAT was inserted in the Epstein-Barr virus episomal vector p220.2 (Yates et al., 313 *Nature* 812, 1985; and Hambor et al., 85 *Proc. Natl. Acad. Sci. USA* 4010, 1988), digested with XbaI and XhoI.

Induction of Expression

Standard techniques were used to test for dexamethasone-inducible transcription, recombinants were transiently transfected in HeLa cells along with pG1B which constitutively expresses the rabbit β-globin gene (Ponglikitmongkol et al., supra) and acts as an internal control, and transcription was monitored by quantitative S1 nuclease analysis.

Specifically, for transient transfections, 5 μg of CAT expression vector or 2 μg of pAL10 derivatives, 1 μg of pG1B internal control plasmid (Kumar et al., supra), for quantitative S1 nuclease analysis or 3 μg or β-galactosidase expression vector pCH220 for CAT assays, and 11–13 μg of BlueScribe (Stratagene) carrier DNA were transfected onto 9 cm plates of HeLa cells in Dulbecco's modified Eagle's medium containing 5% fetal bovine serum at approximately 50% confluency using the calcium phosphate co-precipitation technique (Banerji et al., *Cell* 299, 1981). Dexamethasone (25 nM) was added immediately after transfection and at 24 hours post-transfection. Cells were harvested 44–48 hours after transfection. For stable transfections, HeLa cells were transected with 15 μg of pGRE5/CAT, 1 μg of neomycin resistance gene expression vector pRc-RSV (Invitrogen) and 4 μg of BlueScribe carrier DNA. G418 (1 mg/ml) was added starting 48 hours after transfection and G418-resistant colonies were picked 3–4 weeks later.

To test for dexamethasone-inducible CAT activity, cells from G418-resistant clones were split into duplicate 9 cm plates and treated as indicated with 25 nM dexamethasone for 48 hours prior to harvesting. Alternatively, HeLa cells were transfected with 15 μg of the Epstein-Barr virus episomal vector p220.2-GRES/CAT and 5 μg of BlueScribe carrier DNA. Hygromycin (250 μg/ml) was added 48 hours later for selection.

Induction of CAT activity of the G418-resistant HeLa cell line 19–11 (any equivalent cell line can be used) by progesterone was tested by transfecting cells with 1 μg of human progesterone expression vector hPRO (Kastner et al., 265 *J. Biol. Chem.* 12163, 1990), 3 μg of pCH110 and 16 μg or BlueScribe carrier.

Cells were harvested for CAT assays in 250 μof 0.25M Tris-HCl (pH 7.5) (Webster et al., 54 *Cell* 199, 1988). CAT assays were performed as described by Tora et al., supra. Quantities of extracts derived from transiently transfected cells were normalized for β-galactosidase activity. Quantitative S1 nuclease analysis was performed as described by Ponglikitmongkol et al., supra.

Quantitative S1 nuclease analysis showed that no transcription was observed from the Ad2MLP recombinant lacking GRE sequences either in the absence or presence of dexamethasone, or from any of the GRE-containing recombinants tested in the absence of hormone. The recombinant GRE1 containing a single GRE upstream of the Ad2MLP TATA region did not produce detectable transcription in the presence of dexamethasone. In contrast, dexamethasone-inducible transcription was observed from the Ad2MLP in recombinants containing two or more GREs. Promoters containing five GREs were 8-fold more inducible than those containing only two elements. The promoter of the GRE5 recombinant was also greater than 3-fold more efficient in the presence of dexamethasone than the constitutively active promoter of an Ad2MLP recombinant containing a equivalently positioned SV40 enhancer.

The above results show that introduction of several GREs upstream of the Ad2MLP TATA region creates a promoter which has very low basal activity and is highly inducible in HeLa cells by the endogenous levels of ligand-activated GR. We therefore constructed the two eukaryotic expression vectors based on this promoter, pGRE5-1 and pGRE5-2, containing polylinker sequences in opposite orientations (see FIG.). The polylinker of each vector was inserted between a fragment of rabbit β-globin gene sequence which contains an intron, and a sequence from the SV40 genome containing a polyA addition signal. To test the capacity of these vectors to induce expression of high levels of protein we inserted the bacterial chloramphenicol acetyltransferase (CAT) gene into pGRE5-2 as described above, and introduced the recombinant plasmid into HeLa cells by transient transfection.

Inducible expression of CAT activity by pGRE5-2/CAT was compared to other dexamethasone-inducible CAT expression vectors containing synthetic promoters and to MMTV/CAT, using quantities of extract normalized to the activity of the β-galactosidase internal control.

No induction of CAT activity by dexamethasone was observed in extract of cells transfected with pBLCAT8+ which contains the Herpes Simplex virus thymidine kinase (tk) promoter but no GREs. Insertion of one or two GREs upstream of the tk promoter gave rise to dexamethasone-inducible CAT activity. The induced activity of the GRE2tk promoter was 3-fold higher than that observed with the GRE1tk promoter. Strikingly, transfection of either of two independent preparations of GRE5-2/CAT into HeLa cells in the presence of dexamethasone gave rise to more that 10- and 30-fold more CAT activity than observed with GRE2tkCAT and GRE1tkCAT, respectively. No induction of activity was observed when the CAT gene was inserted in pGRE5-1 in the antisense orientation.

Virtually no dexamethasone-inducible CAT activity was observed in extracts of cells transfected with MMTV/CAT. However, activity was clearly observed if 25-fold more extract was used. Under these conditions, the activity of pGRE5-2/CAT in the presence of dexamethasone is at least 50-fold higher than that of the MMTV/CAT. Moreover, whereas the inducible activity of the MMTV promoter was enhanced more than 5-fold by co-transfection of a glucocorticoid receptor expression vector, the activity of the GRE5 promoter was not significantly affected, indicating that the GRE5 promoter is efficiently inducible by endogenous levels of GR in HeLa cells.

We also compared the activity in HeLa cells of pGRE5-2/CAT to the constitutively active SV40 and cytomegalovirus (CMV) enhancer-based promoters of pSV2-CAT and CMV-CAT and saw that, in the presence of dexamethasone, the pGRE5 promoter was more efficient than either the pSV2 or pCMV promoters. Under these conditions the CMV promoter was as efficient as the induced MMTV promoter. These results demonstrate that high levels of induction by dexamethasone can be obtained when using a promoter composed solely of multiple GREs and a TATA region.

Since the pGRE5 vectors contain a synthetic promoter it is important to verify that they are functional when stably propagated in cells. The pGRE5/CAT plasmid was therefore introduced into HeLa cells by co-transfection with the pRcRSV vector which expresses the neomycin resistance gene. CAT assays of G418-resistant clones expressing dexamethasone-dependent CAT activity were performed. The CAT gene was inserted in pGRE5-1 in the antisense or sense orientation.

Of 22 neomycin-resistant clones, 8 expressed CAT activity. These 8 clones displayed variable levels of background activity and dexamethasone inducibility. The quantities of extract tested correspond to $\frac{1}{250}$th (1 μl) and $\frac{1}{25}$th (10 μl) of total extract from 9 cm plates of cells harvested at 70% confluency (≈2.5 μg and ≈25 μg of protein, respectively). Six clones, 17-4, 18-5, 18-7, 18-8, 19-11 and 20-5, showed a combination of little background activity and high levels of induction in the presence of dexamethasone. Indeed, no CAT activity was visible with extracts of the clone 19-11 not treated with dexamethasone under these conditions.

The GRE5 promoter is strongly inducible by dexamethasone when propagated in the Epstein-Barr virus episomal vector p220.2 (Yates et al., supra; and Hambor et al., supra). Dexamethasone-dependent CAT activity of two independent clones of hygromycin-resistant HeLa cells carrying the GRE5/CAT expression cassette in the Epstein-Barr virus expression vector p2202 was measured. No CAT activity was observed in extracts of cells transfected with p220.2-GRE51-/CAT which carries the CAT gene in the antisense orientation. In contrast, very low background activity and high dexamethasone-inducibility were observed in extracts of cells transfected with p220.2-GRE5-2/CAT which expresses the CAT gene. These results are typical of other clones tested. The levels of activity observed in clones 6 and 7 are comparable to that observed with G418-resistant HeLa clone 19-11.

Induction of the GRE5 promoter by progesterone was also measured. The TAT GRE can confer responsiveness to both glucocorticoids and progesterone in transiently transfected cells when placed upstream of an unresponsive promoter (Tsai et al., 55 Cell 361, 1988), and the progesterone receptor binds to the element in vitro (Tsai et al., supra). We used the HeLa cell line 19-11, which contains GRE5/CAT, to determine if the GRE5 promoter is progesterone responsive in stably transfected cells. HeLa 19-11 cells were treated with 100 nM progesterone for 48 hours prior to harvesting. No CAT activity was observed in 19-11 cells treated or not the progesterone. However, upon transient transfection with the human progesterone receptor expression vector hPRO, progesterone-responsive CAT activity was observed. These results demonstrate that the GRE5 promoter is progesterone responsive in the presence of the progesterone receptor when stably integrated in the HeLa cell genome.

In summary, we have developed a fully defined, synthetic steroid-inducible promoter/expression system that is applicable for the tightly controlled expression of cloned genes in wide variety of cell types expressing glucocorticoid or progesterone receptors, and in cells expressing androgen or mineralocorticoid receptors.

Other embodiments are within the following claims.

We claim:

1. An expression vector adapted for replication in an animal cell comprising a glucocorticoid responsive promoter, said promoter comprising a plurality of at least 5 glucocorticoid response elements (GREs), a viral or mammalian TATA box, and a viral or mammalian initiator element with a transcriptional initiator site located from 20 to 50 bases from said TATA box, said promoter lacking upstream elements which bind nuclear factor I, and said vector further comprising a restriction endonuclease site downstream from said promoter for insertion of DNA to be expressed from said promoter; wherein said DNA is expressed from said vector in an animal cell.

2. The vector of claim 1, wherein said TATA is from 25 to 30 bases from said initiation site.

3. The vector of claim 1, wherein said GREs are upstream from said TATA box.

4. The vector of claim 1, wherein at least two of said GREs are within 100 bases of said TATA box.

5. The vector of claim 1, wherein at least five of said GREs are within 500 bases of said TATA box.

6. The vector of claim 5, wherein said GREs are from 20 to 500 bases apart.

7. The vector of claim 5, wherein said GREs are from 30 to 40 bases apart.

8. The vector of claim 1, wherein each of said GRE comprises at least one half consensus sequence of a GRE able to bind a glucocorticoid, progesterone, androgen or mineralocorticoid receptor.

9. The vector of claim 8, wherein each of said GREs comprises a consensus sequence for a said GRE able to bind a glucocorticoid, progesterone, androgen or mineralocorticoid receptor.

10. A promoter consisting of a plurality of at least five glucocorticoid response elements (GREs), a TATA box, and an initiator site containing a transcriptional initiator site located from 20 to 50 bases from said TATA box, said promoter lacking upstream elements which bind nuclear factor I, wherein said promoter is responsive to ligand-bound glucocorticoid, progesterone, androgen or mineralocorticoid receptor when transiently transfected into cells, when stably integrated within a genome, or when stably propagated in an episomal vector.

* * * * *